United States Patent [19]
Kato et al.

[11] Patent Number: 5,756,823
[45] Date of Patent: May 26, 1998

[54] GLUTATHIONE MONOESTER SULFONATE

[75] Inventors: Sachiko Kato, Kawachinagano; Iwao Chujo, Izumisano; Takehiro Ogasa, Sakai; Masaji Kasai, Fujisawa; Yukiteru Mimura, Shizuoka, all of Japan

[73] Assignee: Kyowa Hakko Kogyo Co., Ltd., Tokyo, Japan

[21] Appl. No.: 852,256

[22] Filed: May 6, 1997

[30] Foreign Application Priority Data

Sep. 5, 1996 [JP] Japan ................................. 8-114740

[51] Int. Cl.$^6$ ................................. C07C 323/41
[52] U.S. Cl. ................................. 560/147
[58] Field of Search ................................. 560/147

[56] References Cited

U.S. PATENT DOCUMENTS 4,709,013  11/1987  Nagano .
5,525,628  6/1996  Nicola et al. .

FOREIGN PATENT DOCUMENTS 61-15870  1/1986  Japan .
9325573  12/1993  WIPO .

OTHER PUBLICATIONS

"Transport of glutathione, as γ-glutamylcysteinylglycyl ester, into liver and kidney," pp. 5258–5260. Sep. 1983 vol. 80 by R. Puri, et al.

Glutathione Monoethyl Ester: High-Performance Liquid Chromatographic Analysis and Direct Preparation of the Free Base Form by E. Campbell, et al pp. 21–25 (1989) vol. 183.

*Primary Examiner*—Michael G. Ambrose
*Attorney, Agent, or Firm*—Antonelli, Terry, Stout & Kraus, LLP

[57] ABSTRACT

The present invention relates to glutathione monoester sulfonate represented by formula (I):

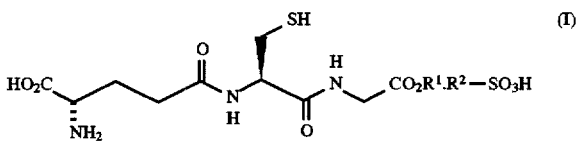

(wherein $R^1$ represent lower alkyl, and $R^2$ represents lower alkyl, or substituted or unsubstituted aryl) which readily crystallizes and has high stability, and a simple process for producing the same. According to the process, the product having high purity can be obtained in high yields.

8 Claims, 3 Drawing Sheets

GLUTATHIONE MONOESTER SULFONATE

BACKGROUND OF THE INVENTION

The present invention relates to glutathione (γ-L-glutamyl-L-cysteinylglycine) monoester sulfonate which readily crystallizes and has high stability, and to a process for producing the same.

Glutathione is known to take part in metabolism, transport of metabolites, protection of cells, and the like, and is used as an antidote for liver, a radioprotective agent, an antidote for agricultural use, and so on. Glutathione is produced in vivo by biosynthesis from glycine, cysteine and glutamic acid. It is necessary to raise the concentration of glutathione in living cells in order to enhance the cell-protecting activity. However, administration of the above-mentioned amino acids in large quantities raises the concentration of glutathione only within certain limits. Administration of glutathione itself does not result in the desired rise in glutathione concentration; because the administered glutathione is decomposed extracellularly, and after absorption of the constituent amino acids into cells, glutathione is reproduced by intracellular biosynthesis. Thus, it has been difficult to raise the concentration of glutathione in cells beyond certain limits.

On the other hand, it is known that glutathione monoester, unlike glutathione, passes into various types of cells at high concentrations and is converted into glutathione through hydrolysis in the tests using animals [(Proc. Natl. Acad. Sci. U.S.A., 80, 5258 (1983)]. Accordingly, glutathione monoester is useful as a readily-absorbable active form of glutathione which is capable of effectively expressing in vivo pharmacological activities of glutathione such as detoxicating activity and radioprotective activity.

With regard to acid addition salts of glutathione monoester formed by ordinary esterification reaction of glutathione, the above-mentioned publication only refers to hydrochloride. However, there is no specific description about the process for producing the salt in the publication. According to U.S. Pat. No. 4,709,013, the hydrochloride cannot be isolated as crystals. Consequently, the purity of the hydrochloride produced is lowered by contamination with glutathione diester which is inevitably formed as a by-product in the esterification process and unreacted glutathione.

U.S. Pat. No. 5,525,628 describes various amino acid addition salts of glutathione monoester and a process for producing the salts. The publication, however, relates to a process for producing the salts from glutathione monoester, and contains no description about a process for producing glutathione monoester itself. That is, in order to obtain the amino acid addition salts of high purity according to the process described in this publication, it is necessary to first obtain glutathione monoester of high purity.

In U.S. Pat. No. 4,709,013, glutathione monoester sulfate and a process for producing the same are described. According to the publication, the sulfate can be obtained as crystals, which facilitates the purification thereof and thus enables the production of glutathione monoester of high purity. However, the publication contains neither description demonstrating the clear crystallizability nor description about the stability upon storage or during the steps of preparation of pharmaceutical compositions. Stability is one of the important properties requisite to a compound which is to be widely used as a drug. There is a report on glutathione monoethyl ester that the precipitate deposited from a sulfuric acid-containing solution with ether is hygroscopic and shows poor stability even when kept at –20° C. [Anal. Biochem., 183, 21 (1989)].

An object of the present invention is to provide glutathione monoester sulfonate which readily crystallizes and has high stability, and a simple process for producing the same by which the product of high purity can be obtained in high yields.

SUMMARY OF THE INVENTION

The present invention relates to glutathione monoester sulfonate represented by formula (I):

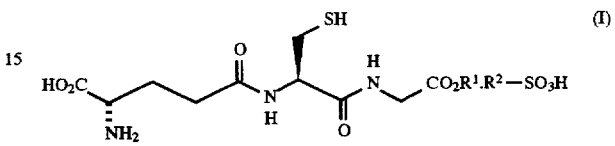

wherein $R^1$ represents lower alkyl, and $R^2$ represents lower alkyl, or substituted or unsubstituted aryl.

The present invention also relates to a process for producing glutathione monoester sulfonate which comprises reacting glutathione with a lower alcohol in the presence of sulfonic acid represented by formula (II):

wherein $R^2$ has the same meaning as defined above.

☐; Glutathione monoethyl ester

◊; Glutathione

○; Glutathione diethyl ester

Δ; Other analogues

DETAILED DESCRIPTION OF THE INVENTION

The compounds represented by formula (I) and formula (II) are hereinafter referred to as Compound (I) and Compound (II), respectively. The same applies to the compounds of other formula numbers.

In the definitions of the groups in formula (I), the lower alkyl and the lower alkyl moiety of the lower alcohol mean a straight-chain or branched alkyl group having 1 to 6 carbon atoms, such as methyl, ethyl, propyl, isopropyl, butyl, isobutyl, sec-butyl, tert-butyl, pentyl, isoamyl, neopentyl, 2-pentyl, 3-pentyl, and hexyl. The aryl means phenyl or naphthyl.

The substituted aryl has 1 to 3 independently selected substituents. An example of the substituent is lower alkyl, which has the same meaning as defined above.

The present invention is described in detail below.

Compound (I) can be prepared according to the following reaction step:

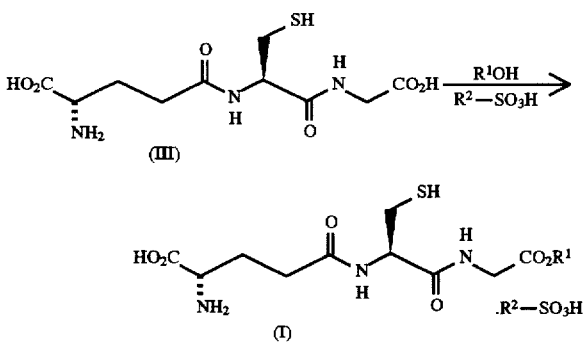

(In the formulae, $R^1$ and $R^2$, have the same meanings as defined above.)

Compound (I) can be obtained by the reaction which proceeds by adding sulfonic acid (II) to a solution or a suspension of glutathione (III) in a large excess of a lower alcohol represented by $R^1OH$ with stirring. As the sulfonic acid (II), those which are commercially available as anhydrides or monohydrates can be used. The sulfonic acid (II) is added in an amount of 1.2 to 3.0 equivalents, preferably 1.5 to 2.0 equivalents, based on glutathione (III). The reaction is carried out at a temperature of $-10°$ C. to the boiling point of the lower alcohol used, preferably at $0°$ to $50°$ C., for 5 minutes to 48 hours.

In the above process, usually, the reaction system temporarily affords a homogeneous solution after the addition of sulfonic acid, and as the reaction proceeds, glutathione monoester sulfonate precipitates as crystals. Accordingly, the reaction product can be isolated by merely separating the crystals by filtration. The obtained crystals may be subjected to purification steps such as washing, drying, and recrystallization.

Compound (I) may be in the form of adducts with water or various solvents, which are also within the scope of the present invention.

The stability of glutathione monoester sulfonate of the present invention on storage is illustrated by the following Test Example.

TEST EXAMPLE 1

Figure 1:
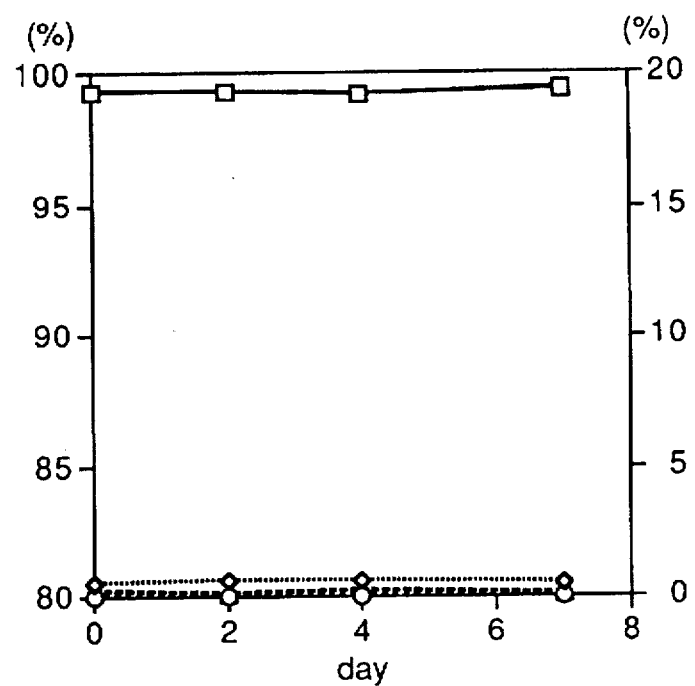
FIG. 1 is a graph showing the stability of glutathione monoethyl ester p-toluenesulfonate on storage. The numbers on the abscissa indicate the passage of time (day), those on the left ordinate indicate the content of glutathione monoethyl ester as determined by high performance liquid chromatography (HPLC) (%), and those on the right ordinate indicate the contents of glutathione, glutathione diethyl ester and other analogues as determined by HPLC (%).
Figure 2:
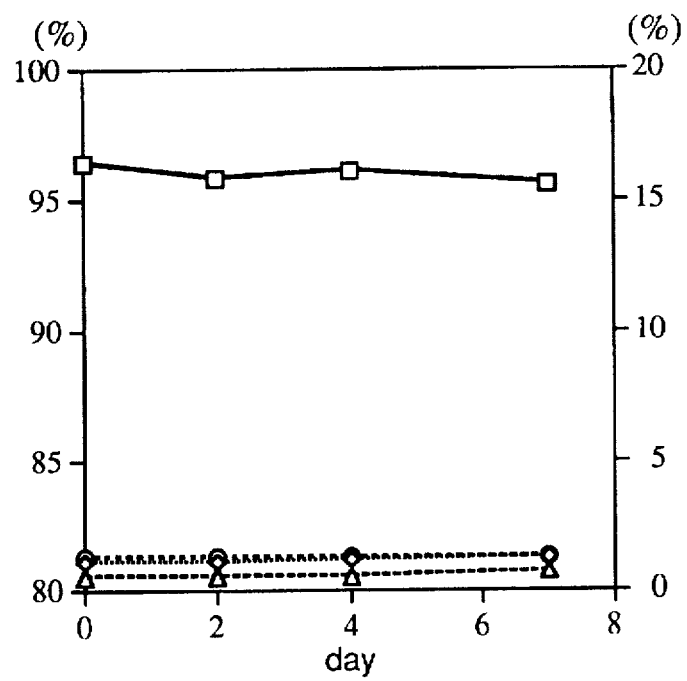
FIG. 2 is a graph showing the stability of glutathione monoethyl ester methanesulfonate on storage. The numbers on the abscissa indicate the passage of time (day), those on the left ordinate indicate the content of glutathione monoethyl ester as determined by HPLC (%), and those on the right ordinate indicate the contents of glutathione, glutathione diethyl ester and other analogues as determined by HPLC (%).
Figure 3:
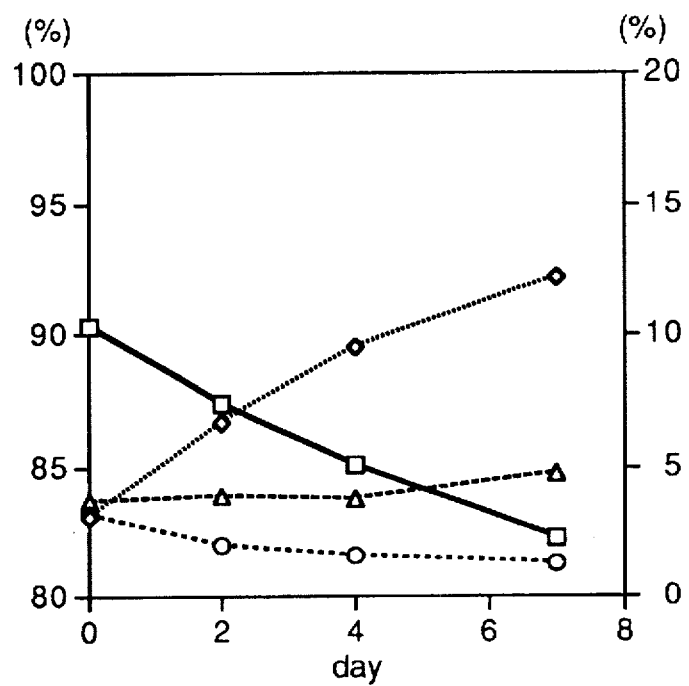
FIG. 3 is a graph showing the stability of glutathione monoethyl ester sulfate on storage. The numbers on the abscissa indicate the passage of time (day), those on the left ordinate indicate the content of glutathione monoethyl ester as determined by HPLC (%), and those on the right ordinate indicate the contents of glutathione, glutathione diethyl ester and other analogues as determined by HPLC (%)

The salts obtained in Examples 1 and 2 and Comparative Example 6 were tested for stability on storage. In the test, the salts were allowed to stand under the atmospheric condition at $40°$ C. at ordinary pressure. The results are shown in FIGS. 1–3.

As is apparent from the figure, HPLC analysis of the sulfate obtained in Comparative Example 6 revealed considerable decomposition of the salt. Hydrolysis proceeded with the passage of time, and after one week, the contents of glutathione, glutathione diethyl ester, and other analogues were found to be 12.17%, 1.30% and 4.76%, respectively, and the glutathione monoethyl ester content was reduced to 82.29%. This result suggests the difficulty in the storage of glutathione monoester sulfate. In contrast, HPLC analysis of the p-toluenesulfonate and methanesulfonate according to the present invention revealed that the salts were not significantly decomposed. For example, according to the analysis of the p-toluenesulfonate after one week, only glutathione (0.51%) was detected as an analogue, glutathione diethyl ester was not detected, and the glutathione monoethyl ester content was little reduced, i.e. 99.4%. This result demonstrates the high stability of the p-toluenesulfonate and methanesulfonate according to the present invention on storage.

Certain embodiments of the present invention are illustrated in the following Examples, Comparative Examples and Reference Examples.

HPLC was carried out under the following conditions.

Column:
YMC AM312 S5 120A ODS
length, 125 mm; diameter, 6 mm
Mobile phase:
acetonitrile/water=15/85
(0.05M phosphate buffer)
Flow rate:
1.0 ml/min.
Detection wavelength:
220 nm
Retention time (min.):
Glutathione monoethyl ester; 4.1
Glutathione; 2.7
Glutathione diethyl ester; 7.2

EXAMPLE 1

Glutathione monoethyl ester p-toluenesulfonate
(ethyl γ-L-glutamyl-L-cysteinylglycinate p-toluenesulfonate)

In 4.55 l of ethanol was suspended 130 g of glutathione, and 105 g (2.0 equivalents) of p-toluenesulfonic acid monohydrate was added to the suspension at $25°$ C. with stirring. The suspension became a homogeneous solution in about 10 minutes, and p-toluenesulfonate of glutathione monoethyl ester (ethyl γ-L-glutamyl-L-cysteinylglycinate) started to precipitate as crystals in about 15 hours. After about 20 hours, the reaction mixture was concentrated to 1.95 l. The crystals precipitated were collected by filtration and washed with 0.13 l of ethanol, followed by drying under reduced pressure to give 180 g of a crude p-toluenesulfonate (yield: 84%., HPLC purity: 96.9%). The obtained crude p-toluenesulfonate (180 g) was dissolved in 1.98 l of ethanol at $70°$ C. The solution was gradually cooled, and then ice cooled to induce crystallization. The crystals precipitated were collected by filtration and washed with 0.18 l of ethanol, followed by drying under reduced pressure to give 153 g of a purified p-toluenesulfonate (yield: 85%, HPLC purity: 99.3%).

Melting Point:
$168°$–$170°$ C.
Elemental Analysis (%):
$C_{12}H_{21}N_3O_6S \cdot C_7H_8O_3S$
Calcd.: C, 44.96; H, 5.76; N, 8.28
Found: C, 44.83; H, 5.63; N, 7.99

IR Absorption Spectrum (KBr, cm$^{-1}$):
3288, 1747, 1730, 1643, 1535, 1236, 690
Specific Rotation:
$[\alpha]_D^{20}=-10.2$ (c=10, water)
NMR Spectrum [D$_2$O, δ (ppm)]:
7.60 (d, J=8.3 Hz, 2H), 7.27 (d, J=8.0 Hz, 2H),
4.46 (t, J=5.7 Hz, 1H), 4.12 (q, J=7.2 Hz, 2H),
3.96 (t, J=6.6 Hz, 2H), 3.92 (d, J=2.6 Hz, 1H),
2.83–2.86 (m, 2H), 2.48–2.54 (m, 2H), 2.30 (s, 3H), 2.09–2.18 (m, 2H), 1.16 (t, J=7.2 Hz, 3H)

EXAMPLE 2

Glutathione monoethyl ester methanesulfonate (ethyl γL-glutamyl-L-cysteinylglycinate methanesulfonate)

In 9.45 l of ethanol was suspended 450 g of glutathione, and 142 ml (1.5 equivalents) of methanesulfonic acid was added to the suspension at 25° C. with stirring. The suspension became a homogeneous solution in about 10 minutes, and methanesulfonate of glutathione monoethyl ester (ethyl γ-L-glutamyl-L-cysteinylglycinate) started to precipitate as crystals in about 20 hours. The reaction was complete in about 24 hours, and the reaction mixture was allowed to stand at room temperature for further 24 hours and then under ice cooling for 24 hours to precipitate crystals. The crystals precipitated were collected by filtration and washed with 0.45 l of ethanol, followed by drying under reduced pressure to give 445 g of a crude methanesulfonate (yield: 70%). The obtained crude methanesulfonate (400 g) was dissolved in 4.40 l of ethanol at 70° C. The solution was gradually cooled, and then ice cooled to induce crystallization. The crystals precipitated were collected by filtration and washed with 0.40 l of ethanol, followed by drying under reduced pressure to give 317 g of a purified methanesulfonate (yield: 79%).

Melting Point:
149°–151° C.
Elemental Analysis (%):
$C_{12}H_{21}N_3O_6S \cdot CH_4O_3S$
Calcd.: C, 36.19; H, 5.84; N, 9.74
Found: C, 36.25; H, 5.69; N, 9.45
IR Absorption Spectrum (KBr, cm$^{-1}$):
3337, 1747, 1730, 1637, 1539, 1232
NMR Spectrum [D$_2$O, δ (ppm)]:
4.46 (t, J=5.7 Hz, 1H), 4.12 (q, J=7.2 Hz, 2H),
3.99 (t, J=6.7 Hz, 2H), 3.93 (d, J=2.6 Hz, 1H),
2.84–2.86 (m, 2H), 2.49–2.55 (m, 2H), 2.71 (s, 3H), 2.11–2.19 (m, 2H), 1.17 (t, J=7.2 Hz, 3H),

COMPARATIVE EXAMPLE 1

Glutathione monoethyl ester sulfate (ethyl γ-L-glutamyl-L-cysteinylglycinate sulfate)

In 40 ml of ethanol was suspended 9.92 g of glutathione, and 2.4 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. The solution was further stirred under ice cooling for 24 hours, but the sulfate was not precipitated as crystals, either.

COMPARATIVE EXAMPLE 2

Glutathione monoethyl ester sulfate (ethyl γ-L-glutamyl-L-cysteinylglycinate sulfate)

In 40 ml of ethanol was suspended 9.92 g of glutathione, and 2.4 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. The solution was further stirred under ice cooling for 48 hours, but the sulfate was not precipitated as crystals, either.

COMPARATIVE EXAMPLE 3

Glutathione monoethyl ester sulfate (ethyl γ-L-glutamyl-L-cysteinylglycinate sulfate)

In 40 ml of ethanol was suspended 9.92 g of glutathione, and 2.4 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. The solution was further stirred under ice cooling for 48 hours, but the sulfate was not precipitated as crystals, either. Then, the solution was concentrated to 25 ml, followed by addition of 10 ml of diethyl ether. However, precipitation of crystals was not still observed.

COMPARATIVE EXAMPLE 4

Glutathione monoethyl ester sulfate (ethyl γ-L-glutamyl-L-cysteinylglycinate sulfate)

In 260 ml of ethanol was suspended 49.6 g of glutathione, and 12 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. The solution was further stirred under ice cooling for 24 hours, but the sulfate was not precipitated as crystals, either.

COMPARATIVE EXAMPLE 5

Glutathione monoethyl ester sulfate (ethyl γ-L-glutamyl-L-cysteinylglycinate sulfate)

In 400 ml of ethanol was suspended 99.2 g of glutathione, and 24 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. The solution was further stirred under ice cooling for 24 hours, but the sulfate was not precipitated as crystals, either.

COMPARATIVE EXAMPLE 6

Glutathione monoethyl ester sulfate (ethyl γ-L-glutamyl-L-cysteinylglycinate sulfate)

In 260 ml of ethanol was suspended 49.6 g of glutathione, and 12 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. The solution was further stirred under ice cooling for 15 hours, but the sulfate was not precipitated as crystals, either. Then, the sulfate of glutathione monoethyl ester obtained in Reference Example was added to the solution as seed crystals. There appeared white turbidity in about 3 hours, and a large amount of crystals precipitated in about 6 hours. The crystals precipitated were collected by filtration and washed with 100 ml of ethanol, followed by drying under reduced pressure to give 22.5 g of a crude sulfate (yield: 36.3%). The obtained crude sulfate (5.00 g) was dissolved in a mixture of 75 ml of ethanol and 75 ml of water under heating, and the solution was gradually cooled to induce crystallization. The crystals precipitated were collected by filtration and washed with 15 ml of ethanol, followed by drying under reduced pressure to give 16.0 g of the desired compound (yield: 71.0%)

COMPARATIVE EXAMPLE 7

Glutathione monoethyl ester sulfate (ethyl γ-L-glutamyl-L-cysteinylglycinate sulfate)

In 400 ml of ethanol was suspended 99.2 g of glutathione, and 24 ml (1.4 equivalents) of sulfuric acid was added dropwise to the suspension with stirring under ice cooling. The suspension became a homogeneous solution in about 30 minutes. Precipitation of sulfate of glutathione monoethyl ester (ethyl γ-L-glutamyl-L-cysteinylglycinate) as crystals was not observed after stirring at room temperature for 24 hours. Then, the sulfate of glutathione monoethyl ester obtained in Reference Example was added to the solution as seed crystals, followed by stirring under ice cooling for 24 hours. The crystals precipitated were collected by filtration and washed with 200 ml of ethanol, followed by drying under reduced pressure to give 39.5 g of a crude sulfate (yield: 31.8%).

REFERENCE EXAMPLE (Desalting and preparation of sulfate: preparation of glutathione monoethyl ester and its sulfate having high purity)

In 0.5 l of water was dissolved 50.0 g of the p-toluenesulfonate obtained in Example 1, and the solution was charged into a column packed with 200 ml of WA30 (weakly basic ion-exchange resin; Mitsubishi Chemical Corporation) previously treated with a 4% aqueous solution of acetic acid. Elution was carried out with water to give 1.0 l of a fraction containing the desired substance. Concentration of this fraction gave 33.0 g of glutathione monoethyl ester of high purity in the free state (yield: 94.6%, HPLC purity: 99.3%). The obtained glutathione monoethyl ester (5.00 g) was suspended in a mixture of 100 ml of ethanol and 10 ml of water, and 0.9 ml (1.2 equivalents) of sulfuric acid was added dropwise to the suspension with stirring under ice cooling. The suspension became a homogeneous solution in about 30 minutes. The solution was further stirred, whereby a sulfate of glutathione monoethyl ester (ethyl γ-L-glutamyl-L-cysteinylglycinate) precipitated as crystals. The crystals precipitated were collected by filtration and dried under reduced pressure to give 1.13 g of the desired pure sulfate (yield: 19.2%).

The results of HPLC analysis of the salts obtained in Examples 1 and 2 and Comparative Example 6 are shown in Table 1.

TABLE 1

|  | Content determined by HPLC (%) | | | |
| --- | --- | --- | --- | --- |
|  | GSH-Et | GSH | GSH-Et$_2$ | Others |
| p-Toluenesulfonate | 99.3 | 0.54 | N.D. | 0.16 |
| Methanesulfonate | 96.4 | 1.12 | 1.30 | 1.18 |
| Sulfate | 90.3 | 3.12 | 3.25 | 3.73 |

GSH-Et: Glutathione monoethyl ester
GSH: Glutathione
GSH-Et$_2$: Glutathione diethyl ester
Others: Other analogues
N.D.: Not detected

What is claimed is:

1. Glutathione monoester sulfonate represented by formula (I)

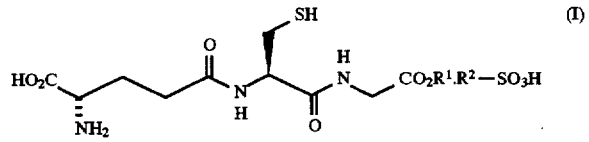

wherein $R^1$ represents lower alkyl, and $R^2$ represents lower alkyl, or lower-alkyl- or unsubstituted aryl.

2. Glutathione monoester sulfonate according to claim 1, wherein $R^1$ is ethyl.

3. Glutathione monoester sulfonate according to claim 2, wherein $R^2$ is methyl.

4. Glutathione monoester sulfonate according to claim 2, wherein $R^2$ is p-toluyl.

5. A process for producing glutathione monoester sulfonate which comprises reacting glutathione with a lower alcohol in the presence of sulfonic acid represented by formula (II):

wherein $R^2$ represents lower alkyl, or lower-alkyl-substituted or unsubstituted aryl.

6. A process according to claim 5, wherein the lower alcohol is ethanol.

7. A process according to claim 6, wherein $R^2$ is methyl.

8. A process according to claim 6, wherein $R^2$ is p-toluyl.

* * * * *